(12) United States Patent
Hartley et al.

(10) Patent No.: US 8,394,136 B2
(45) Date of Patent: Mar. 12, 2013

(54) STENT GRAFT WITH INTERNAL TUBE

(75) Inventors: David Ernest Hartley, Subiaco (AU);
Eric L. G. Verhoeven, Groningen (NL)

(73) Assignees: William A. Cook Australia Pty. Ltd.
(AU); Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 11/632,683

(22) PCT Filed: Jun. 15, 2005

(86) PCT No.: PCT/US2005/021265
§ 371 (c)(1),
(2), (4) Date: Nov. 9, 2007

(87) PCT Pub. No.: WO2005/122962
PCT Pub. Date: Dec. 29, 2005

(65) Prior Publication Data
US 2008/0281399 A1      Nov. 13, 2008

Related U.S. Application Data

(60) Provisional application No. 60/579,958, filed on Jun. 15, 2004.

(51) Int. Cl.
*A61F 2/06* (2006.01)
(52) U.S. Cl. .................................................. 623/1.13
(58) Field of Classification Search ................ 623/1.35, 623/1.13, 1.2, 1.23, 1.15, 1.16, 1.3, 1.31, 623/1.34, 1.12, 1.17–1.22, 1.27–1.29, 1.32, 623/1.33, 1.36–1.54; 606/192, 194, 108
See application file for complete search history.

(56) References Cited

U.S. PATENT DOCUMENTS

| | | | |
|---|---|---|---|
| 5,387,235 A | 2/1995 | Chuter | |
| 5,720,776 A | 2/1998 | Chuter et al. | |
| 6,206,931 B1 | 3/2001 | Cook et al. | |
| 6,319,278 B1 * | 11/2001 | Quinn | 623/1.13 |
| 6,395,018 B1 * | 5/2002 | Castaneda | 623/1.13 |
| 6,454,796 B1 * | 9/2002 | Barkman et al. | 623/1.35 |
| 6,645,242 B1 * | 11/2003 | Quinn | 623/1.16 |
| 6,932,837 B2 * | 8/2005 | Amplatz et al. | 623/1.15 |
| 6,949,121 B1 * | 9/2005 | Laguna | 623/1.35 |
| 6,974,471 B2 | 12/2005 | Van Schie et al. | |
| 2002/0052643 A1 * | 5/2002 | Wholey et al. | 623/1.13 |
| 2002/0116047 A1 * | 8/2002 | Vardi et al. | 623/1.11 |
| 2003/0120332 A1 | 6/2003 | Hartley | |
| 2003/0199967 A1 * | 10/2003 | Hartley et al. | 623/1.13 |
| 2004/0054396 A1 | 3/2004 | Hartley et al. | |
| 2004/0138737 A1 * | 7/2004 | Davidson et al. | 623/1.35 |
| 2004/0254628 A1 * | 12/2004 | Nazzaro et al. | 623/1.13 |
| 2005/0273162 A1 * | 12/2005 | Laguna | 623/1.53 |

FOREIGN PATENT DOCUMENTS

| | | |
|---|---|---|
| WO | WO 98/53761 | 12/1998 |
| WO | WO-03/082153 | 10/2003 |

\* cited by examiner

*Primary Examiner* — Kathleen Sonnett
*Assistant Examiner* — Jocelin Tanner
(74) *Attorney, Agent, or Firm* — Brinks Hofer Gilson & Lione

(57) ABSTRACT

A stent graft (1) with an internal tube (15) extending from the fenestration (11) within and towards an end of the tubular body (3) of the stent graft. An end of the tube remote from the fenestration is flared into a funnel or elliptical shape (17) to facilitate access into the internal tube from a main lumen of the stent graft. The flared portion is fastened (19) to the wall of the stent graft. The flared portion is held open with a resilient wire ring (21).

12 Claims, 2 Drawing Sheets

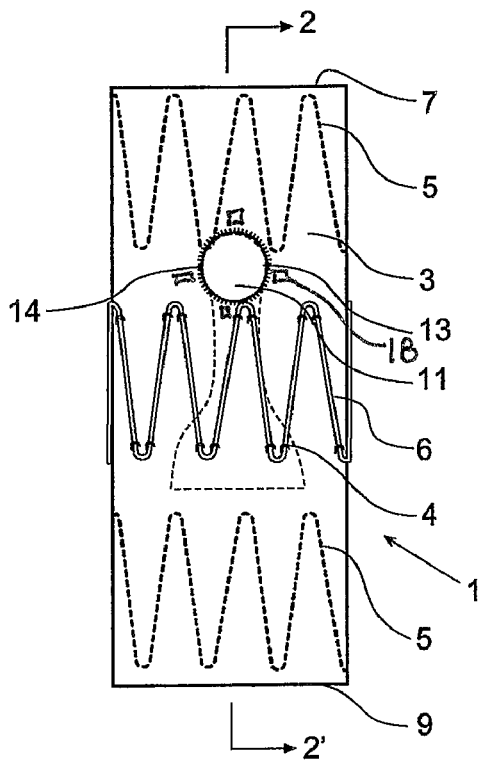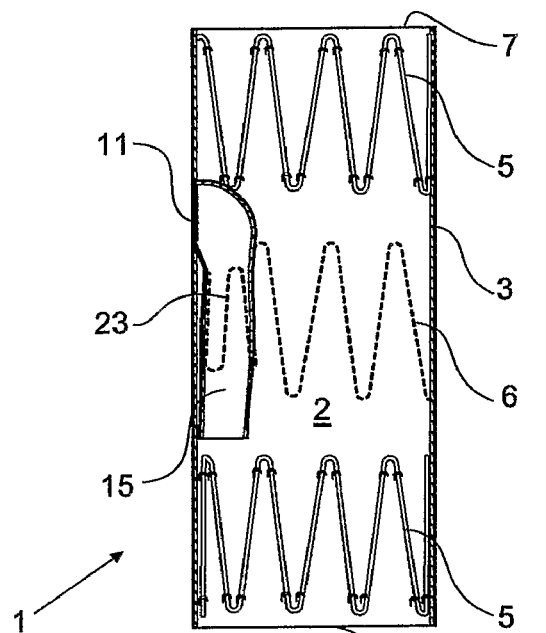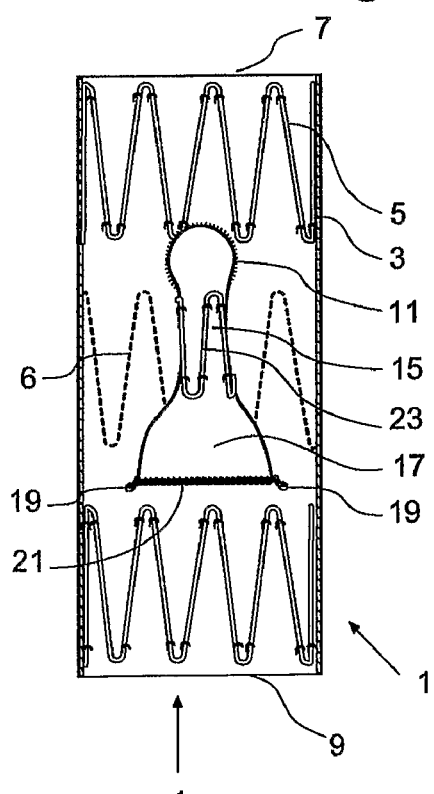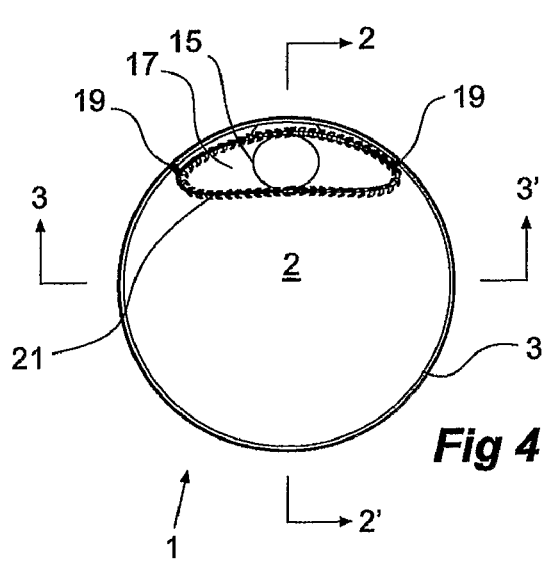

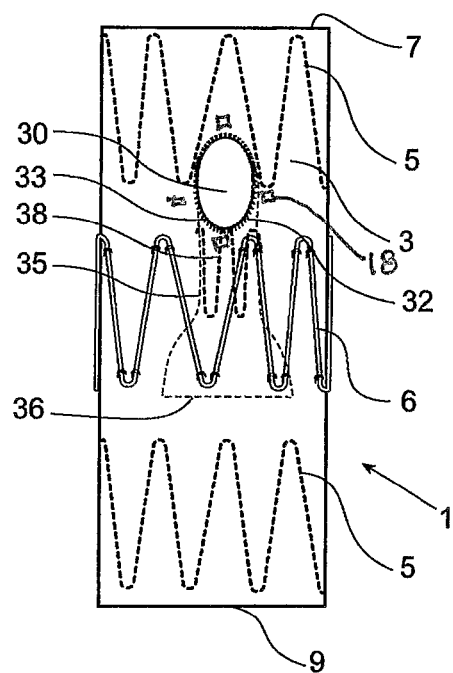
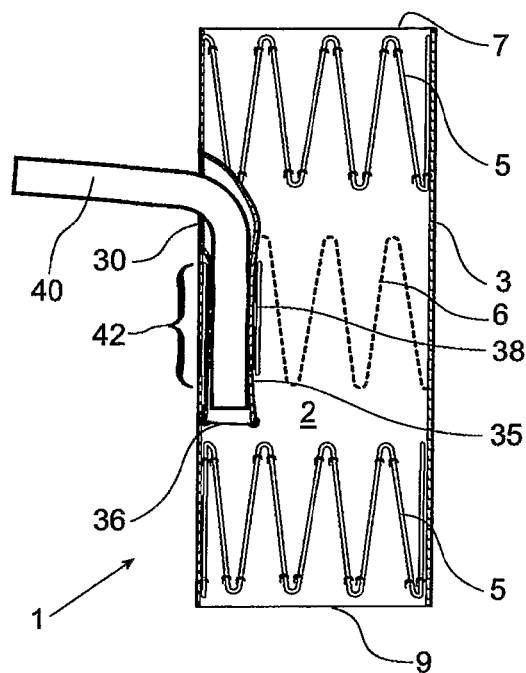
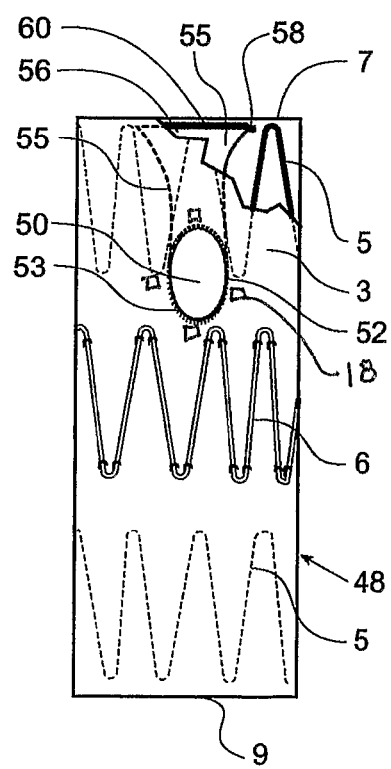

STENT GRAFT WITH INTERNAL TUBE

TECHNICAL FIELD

This invention relates to a stent graft for use with endovascular surgery techniques.

BACKGROUND OF THE INVENTION

Stent grafts for use in human or animal vasculature, such as in the aorta of a patient, are known and where such stent grafts are to be placed in the region of a vessel which has a side branch, it is known to have fenestrations to allow blood flow into the side branch vessel from the stent graft.

There have been proposals for an internal leg on such a stent graft so that an auxiliary branch vessel can be extended from the main stent graft to seal in the internal leg and extend through the fenestration to the side branch vessel.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form, therefore, the invention is said to reside in a stent graft comprising a tubular body of a biocompatible graft material defining a main lumen therethrough; a fenestration in the tubular body; an internal tube extending from the fenestration within and towards an end of the tubular body and being in fluid communication with the main lumen; and an end of the internal tube remote from the fenestration being flared into a funnel shape, whereby to facilitate access into the internal tube from the main lumen.

It will be seen that by this invention where it is necessary to deploy an endovascular device into the internal tube the use of the funnel shape at the opening of the internal tube will assist a practitioner in deploying the endovascular device into the internal tube. Generally a first stage in the deployment of an endovascular device is the deployment of a guide wire, over which an endovascular device can be introduced and the placement of the guide wire into the internal tube can be facilitated by the use of the funnel shaped opening to the internal tube.

Preferably the stent graft includes at least one stent fastened to the graft material to hold the stent graft tube open once it is released from a deployment device. Preferably this at least one stent is a self-expanding stent.

The internal tube can comprise a biocompatible graft material and can include at least one stent such as a self-expanding zig-zag Gianturco stent to hold it open once it is released from a deployment device. Preferably the at least one stent is on the outside of the internal tube so that the internal surface of the internal tube presents a substantially smooth surface for sealing against a branch or extension tube deployed into it.

The internal tube extending inwards from the fenestration may extend to either the proximal or distal end of the stent graft tubular body. The choice of proximal or distal end will depend on which way the practitioner intends to approach the internal tube during the process of deployment of an endovascular device to enter the internal tube.

The funnel shaped end of the tube remote from the fenestration, may be flared into an elliptical shape so that it at least in part fits around the internal surface of the tubular body of the stent graft in to which it is placed so that while it presents a larger opening to enable access of a guide wire or the like it does not present a significant flow reducing feature within the stent graft.

In essence therefore the internal tube may have what may be termed a fishtail shape.

The end of the internal tube remote from the fenestration may be held into a selected funnel or elliptical shape by placement of a reinforcing ring of a resilient wire such as a ring of nitinol wire. The ring of resilient wire may be stitched to material of the internal tube.

When the stent graft is in a constricted state for deployment the resilient wire ring is collapsed but on release the resilient wire ring will open into its selected funnel or elliptical shape.

To ensure that the end of the internal tube remains adjacent to the internal surface of the tubular body of the stent graft, the internal tube may be stitched to the sides of the stent graft for instance at two opposite positions of the flared end. The stitching preferably engages around the reinforcing ring of a resilient wire at the end of the internal tube remote from the fenestration.

The internal tube may have a diameter suitable for sealing of an auxiliary leg tube into it and may have a diameter of six, eight or ten millimeters for instance.

The tubular body of the stent graft may have a diameter in the range of twenty to forty-four millimeters.

The internal tube can include a stent such as a self-expanding zig-zag Gianturco stent on its outside to hold it open once it is released from a deployment device.

The fenestration in the tubular body of the stent graft may also include a ring of a resilient wire such as a nitinol ring around its periphery to hold the fenestration open. Once again the resilient wire ring will collapse within a constraining deployment device but open out into a ring shape when released from the deployment device.

There can be placed radiopaque or similar markers to assist with visualisation of the position of the fenestration and the opening to the internal tube.

The fenestration in the tubular body may be circular or it may be elliptical in shape. The use of an elliptical shape may assist with allowing for degree of mis-alignment between the fenestration in the stent graft and a side vessel.

The fenestration if circular may have a diameter of 6 to 10 millimeters and if elliptical may have a size of from 6 to 10 millimeters wide and from 12 to 20 millimeters long. The internal tube can have a diameter of from 5 to 15 mm opening out to an elliptical or funnel shaped end having a opening of from 10 mm by 5 mm to 20 mm by 10 mm. The length of the internal tube can be from 10 mm to 30 mm and it can have one or two zig zag stents along its length on either the inside or the outside of the tube. Preferably it or they are on the outside of the internal tube so that the inside surface of the internal tube presents a smooth sealing surface for an extension leg placed therein.

The stent graft may have an overall length and diameter determined upon the portion of vasculature into which it is to be deployed. For deployment in the aorta the stent graft may for instance be from 100 to 250 mm long and have a diameter of from 20 to 44 mm. For deployment in it the iliac artery the stent graft may have a length of from 80 to 120 mm long and a diameter of from 12 to 20 mm.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

PCT Patent Publication Number WO98/53761 entitled "A Prosthesis and a Method of Deploying a Prosthesis" discloses an introducer for a prosthesis which retains the prosthesis so that each end can be moved independently. These features and other features disclosed in PCT Patent Publication Number No. WO98/53761 could be used with the present invention and the disclosure of PCT Patent Publication Number No. WO98/53761 is herewith incorporated in its entirety into this specification.

U.S. patent application Ser. No. 10/280,486, filed Oct. 25, 2002 and published on May 8, 2003 as U.S. Patent Application Publication No. US-2003-0088305-A1 and PCT Patent Publication No. WO 03/034948 entitled "Prostheses For Curved Lumens" discloses prostheses with arrangements for bending the prosthesis for placement into curved lumens. This feature and other features disclosed in U.S. patent application Ser. No. 10/280,486, and U.S. Patent Application Publication No. US-2003-0088305-A1 and PCT Patent Publication No. WO 03/034948 could be used with the present invention and the disclosure of U.S. patent application Ser. No. 10/280,486, and U.S. Patent Application Publication No. US-2003-0088305-A1 and PCT Patent Publication No. WO 03/034948 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

U.S. Provisional Patent Application Ser. No. 60/391,737, filed Jun. 26, 2002, U.S. patent application Ser. No. 10/602,930, filed Jun. 24, 2003, and published on Mar. 18, 2004, as U.S. Patent Application Publication No. US-2004-0054396-A1, and PCT Patent Publication No. WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and U.S. Patent Application Publication No. US-2004-0054396-A1, and PCT Patent Publication No. WO 2004/002365 could be used with the present invention and the disclosure of U.S. Provisional Patent Application Ser. No. 60/391,73, U.S. patent application Ser. No. 10/602,930, and U.S. Patent Application Publication No. US-2004-0054396-A1, and PCT Patent Publication No. WO 2004/002365 is herewith incorporated in its entirety into this specification.

U.S. patent application Ser. No. 10/322,862, filed Dec. 18, 2002 and published as U.S. Patent Application Publication No. US2003-0120332, and PCT Patent Publication No. WO 03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as U.S. Patent Application Publication No. US2003-0120332, and PCT Patent Publication No. WO 03/053287 could be used with the present invention and the disclosure of U.S. patent application Ser. No. 10/322,862, filed Dec. 18, 2002 and published as U.S. Patent Application Publication No. US2003-0120332, and PCT Patent Publication No. WO 03/053287 is herewith incorporated in its entirety into this specification.

BRIEF DESCRIPTION OF THE DRAWING

This then generally describes invention but to assist with understanding reference will now be made to the accompanying drawings, which show preferred embodiments of the drawings.

In the drawings:

FIG. 1 shows a first embodiment of stent graft according to the invention;

FIG. 2 shows a cross sectional view of the stent graft shown in FIG. 1 along the line 2-2';

FIG. 3 shows a further cross sectional view of the stent graft shown in FIG. 1;

FIG. 4 shows an end view of the stent graft shown in FIG. 1 and also showing the positions of the cross sectional view 2-2' shown in FIGS. 2 and 3-3' shown in FIG. 3.

FIG. 5 shows an alternative embodiment stent graft according to the invention;

FIG. 6 shows a cross sectional view of the embodiment of stent graft shown in FIG. 5 with a side branch stent graft deployed into the internal leg; and FIG. 7 shows a part cutaway view of an alternative embodiment stent graft according to the invention.

DETAILED DESCRIPTION

Now looking at the drawings and in particular the embodiment shown in FIGS. 1 to 4 it will be seen that the stent graft 1 comprises a tubular body 3 of a bio-compatible graft material. The tubular body 3 defines an internal main lumen 2. The stent graft is depicted having three self-expanding zig zag Gianturco stents 5, 6, however, any different number of stents can be used for the stent graft of the present invention. There is an internal stent 5 at each end of the stent graft and an external stent 6 between the ends. The stent graft has a proximal end 7 and a distal end 9.

Each of the stents is stitched to the graft material by means of stitches 4 of a suture material through the graft material 3.

In between the proximal internal stent 5 and external stent 6 is a fenestration 11. The fenestration 11 is defined by a nitinol ring 13 around its periphery and includes stitching 14 to the graft material.

Extending from the fenestration 11 towards the distal end 9 of the stent graft 1 and through the main lumen 2 is an internal tube 15. At the end of the internal tube 15 remote from the fenestration 11, the tube is flared out into a funnel shape 17 as can be best seen in FIGS. 3 and 4. As can be seen in FIG. 4 it is preferable that the funnel shape is essentially fishtail or elliptical so that it hugs the internal surface of the stent graft tubular body 3 and does not significantly block flow through the main lumen 2. The flared funnel shaped end 17 can be stitched at 19 to the tubular body 3 to hold it in place. A nitinol ring 21 is provided to hold the flared funnel shaped end open once the stent graft has been released.

The internal tube 15 has an external stent 23 to assist with holding the internal tube 15 open once the stent graft has been released and to provide a substantially smooth internal surface for sealing against a branch or extension tube deployed into it.

FIGS. 5 and 6 show an alternative embodiment stent graft according to the invention with a side branch stent graft deployed into the internal leg. The embodiment of stent graft shown in FIGS. 5 and 6 is substantially similar to that shown in FIGS. 1 to 4 and the same reference numerals will be used for corresponding items.

The stent graft 1 comprises a tubular body 3 of a biocompatible graft material. The tubular body 3 defines an internal main lumen 2. The stent graft is depicted having three self-expanding zig zag Gianturco stents 5, 6, however, any different number of stents can be used for the stent graft of the present invention. There is an internal stent 5 at each end of the stent graft and an external stent 6 between the ends. The stent graft has a proximal end 7 and a distal end 9.

In this embodiment the fenestration 30 is oval or elliptical in shape with its longer axis aligned with the long axis of the stent graft 1. The use of an elliptical shape assists with allowing for degree of mis-alignment between the fenestration in the stent graft and a side vessel in a vessel such as the aorta into which it is deployed. It will be noted that the fenestration fits between the struts of the proximal internal stent graft 5. Once again the fenestration 30 includes a ring 32 of a resilient wire such as nitinol around its periphery and is stitched by means of stitching 33 to the tubular body 3.

In a similar manner to the early embodiment an internal tube 35 extends to a flared end 36 within the tubular body 3. The internal tube 35 has an external self expanding stent 38 to assist with holding the internal tube 35 open once the stent graft has been released and to provide a substantially smooth internal surface for sealing against a branch or extension tube deployed into it.

FIG. 6 shows the stent graft of FIG. 5 after the deployment of an auxiliary leg graft 40 through the fenestration 30 and extending down the internal tube to seal into the internal leg 35 in the region indicated by the reference numeral 42 to provide a fluid tight seal from the main lumen of the stent graft 1 into the auxiliary leg graft 40. It will be noted that the auxiliary leg graft 40 does not seal in this embodiment in the fenestration 30.

FIG. 7 shows a part cutaway view of an alternative embodiment of stent graft according to the invention. The embodiment of stent graft 48 shown in FIG. 7 is substantially similar to that shown in FIGS. 1 to 4 and the same reference numerals will be used for corresponding items.

The stent graft 1 comprises a tubular body 3 of a biocompatible graft material. The tubular body 3 defines an internal main lumen 2. The stent graft is depicted having three self-expanding zig zag Gianturco stents 5, 6, however, any different number of stents can be used for the stent graft of the present invention. There is an internal stent 5 at each end of the stent graft and an external stent 6 between the ends. The stent graft has a proximal end 7 and a distal end 9. The graft material tube 3 is shown partially cut away at the proximal end 7.

In this embodiment the fenestration 50 is oval or elliptical in shape with its longer axis aligned with the long axis of the stent graft 1. It will be noted that the fenestration fits between the struts of the proximal internal stent graft 5. Once again the fenestration 50 includes a ring 52 of a resilient wire such as nitinol around its periphery and is stitched by means of stitching 53 to the tubular body 3. In a similar manner to the early embodiments an internal tube 55 extends from the fenestration 50 to a flared end 56 within the tubular body 3. In this embodiment the flared tube 55 extends towards the proximal end 7 of the stent graft 1. The end of the internal tube 55 remote from the fenestration can be seen in the cutaway portion of the stent graft material tube 3. The flared end 56 can be stitched at 58 to the tubular body 3 to hold it in place. A nitinol ring 60 is provided to hold the flared end open once the stent graft has been released.

If the stent graft 48 shown in FIG. 7 was deployed into the common iliac artery, for instance, with the fenestration adjacent the internal iliac artery, then the internal tube could open towards the aortic bifurcation. Access to the internal tube may then be possible by deployment through the contra-lateral iliac artery over the aortic bifurcation.

The stent graft also includes a plurality of well-known radiopaque markers 18 around the fenestration to radiographically visualize the position of the fenestration and the opening to the internal tube.

Throughout this specification various have been given as to the scope of the invention but the invention is not limited to any one of these but may reside in two or more of these combined together. The examples are given for illustration only and are not for limitation.

The invention claimed is:

1. A stent graft comprising a tubular body of a biocompatible graft material defining a main lumen therethrough, the tubular body comprising an internal surface, a fenestration in the tubular body, the fenestration in the tubular body of the stent graft comprising a ring of a resilient wire around its periphery whereby the fenestration is held open when the stent graft is released from a deployment device, an internal tube extending from the fenestration within and towards an end of the tubular body and being in fluid communication with the main lumen, the internal tube being fastened to the tubular body around the periphery of the fenestration, the internal tube having at least one self expanding stent thereon, the at least one stent being on the outside of the internal tube, whereby the internal tube is held open when the stent graft is released from a deployment device, only an end portion of the internal tube remote from the fenestration being flared and comprising a funnel shaped end portion, the funnel shaped end portion comprising an elliptical shape in cross section, the funnel shaped end portion engaged against only part of the internal surface of the tubular body leaving the main lumen open to fluid flow, the funnel shaped end portion comprising a reinforcing ring of a resilient wire and comprising stitches engaging it to the internal surface of the tubular body of the stent graft, whereby the end of the internal tube remote from the fenestration remains adjacent to part of the internal surface of the tubular body of the stent graft and facilitates access into the internal tube from the main lumen.

2. A stent graft as in claim 1 wherein the internal tube comprises a biocompatible graft material.

3. A stent graft as in claim 1 wherein the internal tube extending from the fenestration extends to a proximal end of the tubular body.

4. A stent graft as in claim 1 wherein the internal tube extending from the fenestration extends to a distal end of the tubular body.

5. A stent graft as in claim 1 wherein the ring of resilient wire is nitinol wire.

6. A stent graft as in claim 1 wherein the internal tube has a diameter in the range of from six to ten millimeters.

7. A stent graft as in claim 1 wherein the tubular body of the stent graft has a diameter in the range of 20 to 44 millimeters.

8. A stent graft as in claim 1 further comprising radiopaque markers whereby visualization of the position of the fenestration and an opening to the internal tube is assisted.

9. A stent graft as in claim 1 wherein the fenestration in the tubular body is circular in shape.

10. A stent graft as in claim 9 wherein the fenestration has a diameter of from 6 to 10 millimeters.

11. A stent graft as in claim 1 wherein the fenestration in the tubular body is elliptical in shape.

12. A stent graft as in claim 11 wherein the fenestration has a size of from 6 to 10 millimeters wide and 12 to 20 millimeters long.

* * * * *